US007856080B2

United States Patent
Klingenbeck-Regn

(10) Patent No.: US 7,856,080 B2
(45) Date of Patent: Dec. 21, 2010

(54) METHOD FOR DETERMINING A DEFINED POSITION OF A PATIENT COUCH IN A C-ARM COMPUTED TOMOGRAPHY SYSTEM, AND C-ARM COMPUTED TOMOGRAPHY SYSTEM

(75) Inventor: Klaus Klingenbeck-Regn, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 67 days.

(21) Appl. No.: 12/316,379

(22) Filed: Dec. 11, 2008

(65) Prior Publication Data

US 2009/0161821 A1   Jun. 25, 2009

(30) Foreign Application Priority Data

Dec. 19, 2007   (DE) .................. 10 2007 061 284

(51) Int. Cl.
*A61B 6/00*   (2006.01)
(52) U.S. Cl. ........................................ 378/20; 378/205
(58) Field of Classification Search .................. 378/20, 378/195, 205, 901; 5/601
See application file for complete search history.

(56) References Cited

U.S. PATENT DOCUMENTS 6,309,103 B1   10/2001   Sano
7,197,107 B2 *   3/2007   Arai et al. ..................... 378/20
2007/0167721 A1   7/2007   Pfister et al.

FOREIGN PATENT DOCUMENTS

DE   102005059804   7/2004

* cited by examiner

*Primary Examiner*—Jurie Yun

(57) ABSTRACT

For facilitating the optimal positioning of a patient resting on the couch of a C-arm computed tomography system, an input is received, via individual pixels or areas of pixels selected in a predetermined image data set, thus enabling the area of interest to be highlighted. Image data of the patient resting on the couch is acquired. These two processes together make it possible to calculate the position, relative to the couch, of a marked-out point that is to coincide with the isocenter for the rotation of the C-arm, and from this at least one coordinate that serves to define the position of the couch can be derived. If this coordinate is displayed, a doctor performing the treatment can move the couch to the appropriate position by hand. The couch can also be designed to be automatically movable by electric motors after determining the coordinate.

9 Claims, 2 Drawing Sheets

METHOD FOR DETERMINING A DEFINED POSITION OF A PATIENT COUCH IN A C-ARM COMPUTED TOMOGRAPHY SYSTEM, AND C-ARM COMPUTED TOMOGRAPHY SYSTEM

CROSS REFERENCE TO RELATED APPLICATIONS

This application claims the benefits of German application No. 10 2007 061 284.4 filed Dec. 19, 2007 and is incorporated by reference herein in its entirety.

FIELD OF INVENTION

The invention relates to a method for determining a defined position of a couch upon which a patient rests, with the couch belonging to a C-arm computed tomography system. Through the defined position, the patient is to be positioned such that an area of the patient's body that is of interest, in particular a specified organ, is located in the so-called isocenter of the C-arm of the C-arm computed tomography system. Once the couch has been brought to the defined position a series of x-ray images can be captured, with the C-arm being rotated about the said isocenter between the capture of the individual x-ray images.

BACKGROUND OF THE INVENTION

Patient couches in C-arm computed tomography systems are generally realized such that certain body parts can be imaged with little effort, in particular without a considerable movement of the couch from its standard position. This is the case for example when imaging the spinal column. In contrast when imaging certain organs, allowance must be made for the position of these organs within the patient's body. For example if the liver of a patient is to be imaged, the couch must be brought to a defined position such that the isocenter of the C-arm of the C-arm computed tomography system coincides directly in the liver. Achieving this state is not very straightforward. Usually an operator, who is frequently the doctor performing the treatment, has to displace the couch by hand and thereby attempt to guess the optimal position as far as possible, and then gradually reach that position by trial and error. This method is time-consuming and the doctor performing the treatment possibly has to capture a fairly large number of x-ray images (so-called projections) in order to correct the current position of the couch with the aid of a view of the area of the patient that is of interest in the x-ray images.

U.S. Pat. No. 6,309,103 B1 describes an x-ray imaging device with independent movement apparatuses for the patient couch on the one hand and for an x-ray radiation source and an x-ray radiation detector on the other hand, with the latter together being rotatable about the patient. The x-ray images of the patient are displayed on a screen. Using a computer mouse the doctor can then select the area of the patient that he wishes to examine.

The device furthermore has a calculating unit which, on the basis of at least two images of the patient captured by the x-ray device from two different directions, calculates the position of the area being observed in relation to the center of rotation of the x-ray radiation source and the x-ray radiation detector. It further consists of a control unit by means of which the movement apparatuses can be controlled.

The publication DE 10 2005 059 804 A1 discloses an image correction method for imaging during a medical intervention. A tomographic 3D image of a target area of the intervention is recorded while one or several medical instruments are located in the target area. These instruments remain in the target area during the intervention, and 2D x-ray images of the target area are recorded and registered with the 3D image, with the 2D/3D registration being adjusted in real time for each 2D image. The 2D images are then each overlaid with views of the 3D image that match up from a perspective view.

SUMMARY OF INVENTION

The object of the invention is to facilitate the determination of a defined position of a patient couch in a C-arm computed tomography system.

The object is achieved by a method and by a C-arm computed tomography system having features in accordance with the claims.

The inventive method thus comprises the following steps:

a) Receiving an input by means of the C-arm computed tomography system for initiating at least one x-ray image recording by means of the C-arm computed tomography system and performing x-ray image recording steps by means of the C-arm computed tomography system for receiving image data that shows the patient resting on the couch, b) Receiving an input by means of which, in an image data set captured in advance with a system that differs from the C-arm computed tomography system, one individual pixel, individual pixels, one area of pixels or individual areas of pixels can be selected, with this image data set captured in advance being registered with the image data received in step a), such that a relationship can be created between the selected individual pixel or the selected individual pixels or the selected area of pixels or the selected areas of pixels and an individual pixel, individual pixels, one area of pixels and/or or areas of pixels, which is/are defined as the image data received in step a).

c) Calculating the defined position, relative to the couch, of a point that is to coincide with the isocenter for rotation of the C-arm on the basis of the image data received in step a) on the one hand and the input received in step b) on the other hand, taking into account the created relationship to the image data received in step a), and deriving therefrom at least one coordinate that serves to define the position of the couch.

By means of the image data received through step a) the unit of the C-arm computed tomography system that performs the calculating step c) can detect the position of the patient relative to the couch. Through the input received in step b) the organ that is of interest is preferably selected, for example any pixel that belongs to the organ is highlighted with the aid of a computer mouse. On the basis of so-called segmenting (image recognition) a computer intelligence can then derive the contours of the organ and select an optimal point in the organ that is to coincide with the isocenter of the C-arm computed tomography system. By means of this input an entire area of pixels can also be selected, for example a subarea of an organ, or the contours of the organ can be specified through this input. Through this input it is also possible to specify directly the point in the organ that is to coincide with the isocenter. The input effects a selection of one or more pixels or one or more areas of pixels in the patient system. The image data received in step a) makes it possible to translate from the patient system to the system of the couch and from the overview it is then possible to calculate the point in c) and derive therefrom how the couch has to be moved.

Following on from existing systems, provision can be made for one operator to move the couch. After the calculating step, a step should follow in which such an operator is notified of all the calculated coordinates that specify the position of the couch. A visual display of the coordinates is preferably selected, but an acoustic notification through speech output is also possible, and the operator could even receive guidance through haptic signals, for example on a joystick, as to how they are to move the couch.

In a particularly convenient version the couch can be moved by at least one electric motor, and following calculation of the coordinate(s) in step c) the couch is then moved automatically to a or the position specified by the calculated coordinate(s). If three coordinates are calculated, then one position has been specified precisely. It is also possible to dispense with a calculation of the height coordinate and specify merely the lateral displacement of the couch. The calculated coordinates then specify several positions that differ in their height coordinate, and it may then still be necessary for the doctor to select the correct height coordinate by hand. The doctor is then relieved of a considerable amount of work adjusting the lateral coordinates, and selecting the height coordinate is generally easier to accomplish than selecting the lateral coordinates.

If certain of the patient's organs are of particular interest, x-ray image recording systems that depict these organs especially well are available. It is then also expedient to highlight the input to be received in step b) in an image data set of this kind that optimally depicts the organ concerned. An image data set of this kind is then captured in advance with a system that differs from the C-arm computed tomography system. So that the highlighting that takes place in the patient system can also be related to the couch system, a step must be performed in which this image data set captured in advance is registered with the image data to be received in step a). The term "registering" is known to mean the relating of image data sets to one another with correct positional and dimensional information, which means that an instruction for mapping from one image data set to the other image data is determined. The calculating step c) can then be performed with the aid of this mapping instruction.

For the purposes of registration it is sufficient in step a) to capture just two individual x-ray images (projections) with the C-arm computed tomography system, if for example a 3D image data set has been received in advance with the aid of a conventional computed tomography system or a nuclear magnetic resonance system. What is shown by these projections should expediently be as different as possible, which is the case in particular if the angularity of the C-arm between the two x-ray images differs by approximately 90°, i.e. within a range of 80° to 100° and preferably between 85° and 95°.

In lieu of two individual images, one so-called 3D topogram can also be captured in step a). Here a three-dimensional data set is acquired, but an extremely low dose is used. The dose must be sufficiently large to make the spinal column of the patient visible so that the registration method mentioned above can be performed. In this case it is not necessary for the image data captured in step a) to adequately depict the patient's organ that is of interest, since the input received in step b) is received with the aid of an image data set that is particularly well suited for this purpose.

The C-arm computer system according to the invention naturally has a C-arm, the purpose of which is to enable a patient couch to be moved to different positions. Furthermore the C-arm computed tomography system has a control unit which, in accordance with the invention, should be designed to receive inputs and, on the basis of said inputs, calculate at least one coordinate that specifies a defined position of the patient couch.

The control unit can be operated by a suitable program, for example a program that is stored in a separate memory. Preferably not just one image data set can be captured by the C-arm computed tomography system itself, but instead image data sets captured by other systems can be transferred to the C-arm computed tomography system, and in order to make the method particularly easy to perform, the C-arm computed tomography system should enable the receiving of an input within the meaning of step b) of the method according to claim 1, for example via a mouse control that allows a doctor performing the treatment to highlight on an image, for example by a simple mouse click, individual pixels or areas of pixels shown on a screen of the C-arm computed tomography system that are based on the predetermined image data set.

The control unit is expediently designed not only to manage image data captured with a system that differs from the C-arm computed tomography system; rather, it should also register said image data with image data captured by the C-arm computed tomography system. The inventive method is then made possible in a preferred embodiment as described above.

In a preferred embodiment, in particular if the couch is not movable by means of motors, a screen of the C-arm computed tomography system can be used to display the calculated coordinates to an operator, with this step being controlled by the control unit that also calculates the coordinates.

In the context of the invention it is also particularly expedient to equip the C-arm computed tomography system with a patient couch that can be moved by (electric) motors actuated by the control unit. The control unit can then be designed to actuate the electric motors automatically such that the patient couch is then moved to a or the position specified by the calculated coordinate(s).

BRIEF DESCRIPTION OF THE DRAWINGS

Preferred embodiments of the invention will now be described with reference to the drawing, in which.

DETAILED DESCRIPTION OF INVENTION

Figure 1:
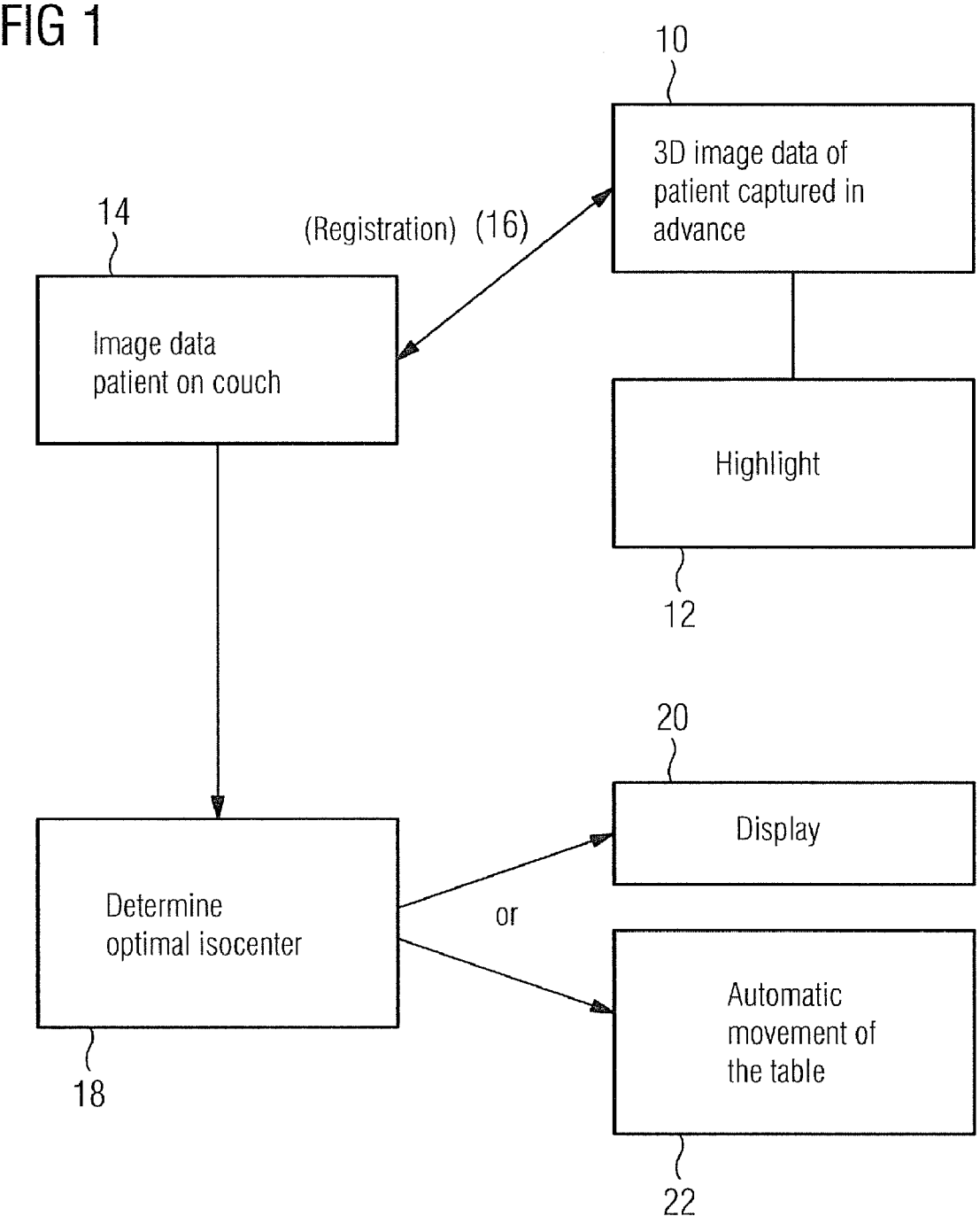
FIG. 1 is a diagram showing the steps involved in an embodiment of the inventive method.

In an embodiment of a method, an area that is of interest, for example a specific organ, of a patient is to be depicted with the aid of a C-arm computed tomography system. The C-arm computed tomography system is to comprise a couch (and/or a table) on which the patient is to be positioned. The couch is to be brought to an optimally defined position so that the so-called isocenter of the C-arm computed tomography system, about which the C-arm rotates when capturing a series of x-ray images, is located where possible in the area that is of interest in the patient.

In a preferred embodiment of the invention, prior to bringing the patient into the C-arm computed tomography system, i.e. on to the said table, the patient is moved to another mapping system and step 10, according to which image data is acquired from the patient, is performed. A particularly convenient computed tomography system, or a nuclear magnetic resonance (MRI, Magnetic Resonance Imaging) system, for example, can be used. The image data captured in step 10 should enable a doctor to identify sufficiently well the area that is of interest in the patient, in other words even a specific organ, and at this point the doctor should provide an input in accordance with step 12 in order to highlight one or several pixels or an entire area of pixels in the image data captured in step 10. It is thus possible to specify in the patient system the point that is to coincide with the isocenter of the C-arm.

However a relationship of the patient to the C-arm computed tomography system, in particular to the table, must now be created. Image data of the patient resting on the table is accordingly captured in step 14. In a first variant exactly two x-ray images of the patient are made, for example an AP image (in which AP stands for "anterior-posterior", in other words the patient is irradiated from the front to the back, i.e. through the breast), and with the second recording being a lateral recording. Both recordings should depict anatomical structures with the aid of which positioning can be performed particularly easily. The spinal column of the patient is particularly suited to this purpose, since it is shown with a high level of contrast in x-ray images.

A complete 3D topogram can be captured in step 14, i.e. a series of 2D x-ray examinations of the patient with an extremely low dose, with the 2D x-ray images as a whole providing a three-dimensional information source. Even with an extremely low dose the spinal column is sufficiently clearly visible.

Now, once a relationship has been created between the patient system and the patient couch by means of the capture of image data of the patient on the table in step 14, the relationship between the highlighting in the patient system and this couch must also now be created. A registration step 16 is performed for this purpose. In the event that two x-ray images were captured in step 14, the registration takes place in two stages, with more or less one 2D/3D registration being performed in each individual step. In the event that a 3D topogram was captured in step 14, a simple 3D/3D registration can be performed.

On the basis of the highlighting, a control unit of the C-arm computed tomography system can now identify a marked-out point that is defined relative to the patient couch. This means that an optimal isocenter is identified relative to the table, cf. step 18. This isocenter does not generally coincide immediately with the actual isocenter of the C-arm of the C-arm computed tomography system, and so the table must be moved. If the table can be moved by hand, it should be ensured that the displacement position can be defined by a specific coordinate, preferably in three dimensions. This can be made possible through the use of a simple measuring tape that is affixed to a mount relative to which the table can be moved. In this case, as a continuation of the previous method, a display appears on one screen of the C-arm tomography system in accordance with step 20, for example simply the numerical values of said coordinates. An operator will then know the position to which they have to move the couch such that the area that is of interest in the patient, as indicated by the highlighting in step 12, is positioned so that it coincides with the isocenter of the C-arm. It is also possible to use a C-arm computed tomography system in which the patient table can be moved automatically. Following the determining step 18 the table can be moved automatically by the control unit of the C-arm computed tomography system in accordance with step 22.

In both cases the result of the inventive method is that the patient is optimally positioned relative to the C-arm, such that the area that is of interest in the patient is optimally imaged.

According to a modified embodiment of the method, which is not the subject matter of the present invention, the prior capture of a 3D image data set with the aid of an image recording system that differs from the C-arm x-ray computed tomography system is dispensed with for specific reasons, for example because it would be too costly and/or time-consuming. In this case the area that is of interest must be determined exclusively on the basis of image data acquired with the C-arm computed tomography system. Thus in accordance with step 14' a 3D image data set of the patient resting on the table is acquired, for example a 3D topogram. Unlike in the case of FIG. 1, it is insufficient here merely to image predetermined structures in the patient, such as the spinal column; instead the organ that is of interest must be sufficiently well imaged. The 3D topogram can then no longer necessarily be captured with an extremely low dose, but instead merely with a dose per projection that is not quite as high as that used for individual x-ray images.

Figure 2:
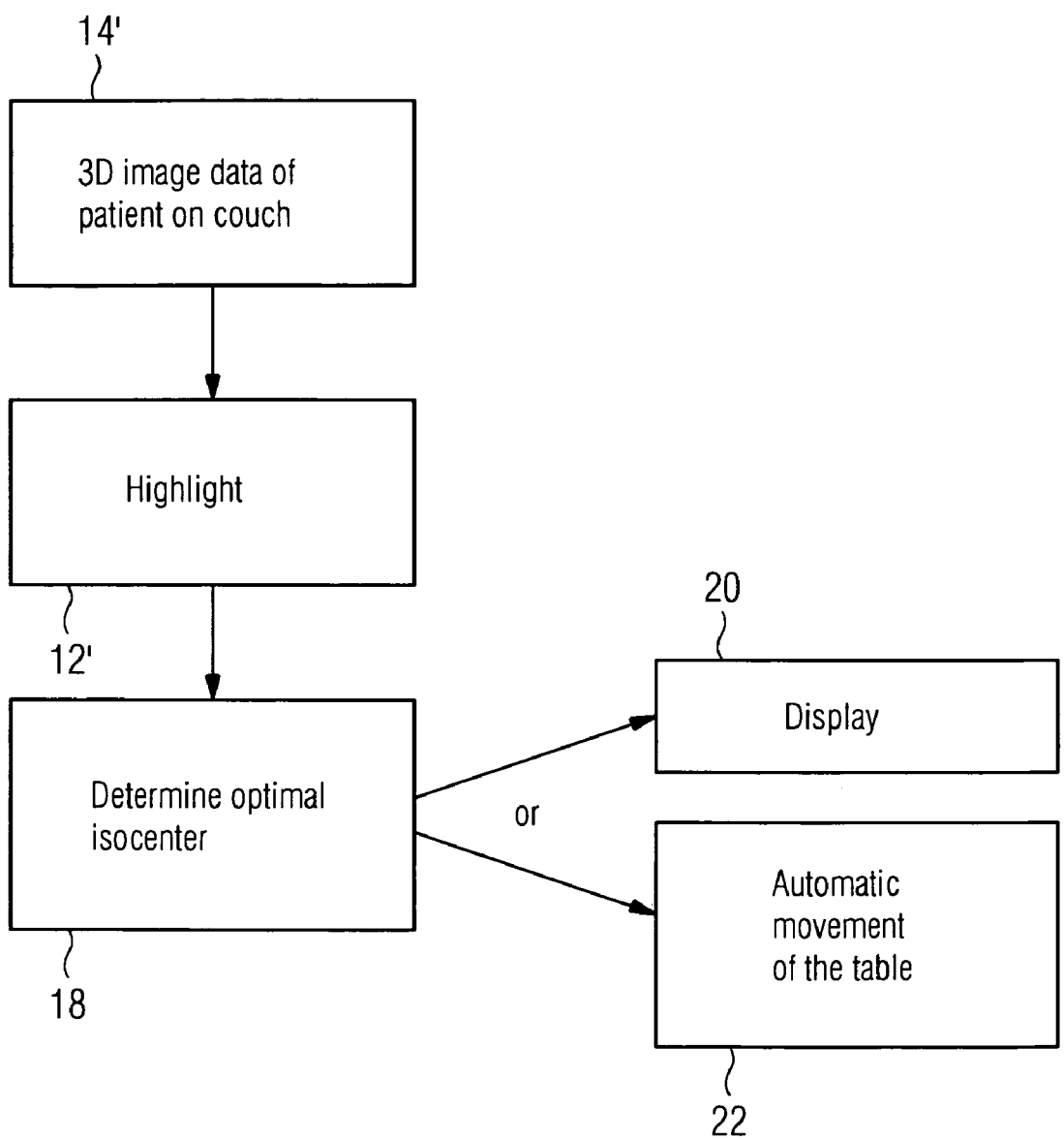
FIG. 2 is a diagram showing the steps of a method other than the inventive method.

Following step 14' a step is performed in which an area that is of interest in the patient is highlighted by the doctor performing the treatment. This step is shown in FIG. 2 as 12', since it differs from the step 12 shown in FIG. 1 insofar as 3D image data is used here that is not the 3D image data captured in advance. As the 3D image data captured in step 14' is not necessarily of such a high quality as the 3D image data captured in advance with a different image recording system, step 12' is not quite as easy to perform as step 12 in FIG. 1. By contrast it is advantageous that one registration step is not required, since the highlighting is performed directly relative to the patient couch system. Step 18 for determining the optimal isocenter, which includes calculating a coordinate that serves to define the position of the couch (preferably at least two lateral coordinates and particularly preferably all three coordinates, i.e. also including the height coordinate) can then be performed directly and, as is the case for the preferred embodiment of the invention, this step is followed alternatively by a display of these coordinates in accordance with step 20, or by the automatic movement of the table in accordance with step 22.

The invention claimed is:

1. A method for determining a defined position of a C-arm computed tomography system couch that a patient rests upon, and with the position of the C-arm being determined such that, once the couch has been brought to the defined position, a series of x-ray images are captured for which, between the capture of the individual x-ray images, a C-arm of the C-arm computed tomography system is rotated about an isocenter, comprising:

receiving an input via the C-arm computed tomography system that initiates at least one x-ray image recording by the C-arm computed tomography system;

performing x-ray image recording steps by the C-arm computed tomography system to receive x-ray image data of the patient resting on the couch;

receiving an image data set of the patient captured in advance by an imaging system that differs from the C-arm computed tomography system, where an area of interest of the patient is selected;

registering the image data set captured by the different imaging system with the x-ray image data received by the C-arm computed tomography system for creating a relationship between the area of interest in the image data set and in the x-ray image data;

calculating the defined position, relative to the couch, of a point that is to coincide with the isocenter for rotation of the C-arm based on the registration; and deriving at least one coordinate defining the position of the couch from the calculation.

2. The method as claimed in claim 1, wherein an operator is notified of all the calculated coordinates that specify the position of the couch.

3. The method as claimed in claim 1, wherein the couch is moved by at least one electric motor and the couch is moved automatically to the position specified by the calculated coordinate(s).

4. The method as claimed in claim 3, wherein the image data received by the C-arm computed tomography system comprises two x-ray images captured at differing angularities of the C-arm between 80° and 100°.

5. The method as claimed in claim 3, wherein the image data received by the C-arm computed tomography system comprises two x-ray images captured at differing angularities of the C-arm between 85° and 95°.

6. The method as claimed in claim 3, wherein the image data received by the C-arm computed tomography system is a 3D topogram.

7. A C-arm computed tomography system for capturing x-ray image data of a patient, comprising:
   a C-arm;
   a movable patient couch that moveable to different positions; and
   a control unit, designed and configured
   to receive an image data set of the patient captured in advance by an imaging system that differs from the C-arm computed tomography system, where an area of interest of the patient is selected,
   to register the image data set captured by the different imaging system with the x-ray image data captured by the C-arm computed tomography system for creating a relationship between the area of interest in the image data set and in the x-ray image data,
   to calculate an defined position, relative to the couch, of a point that is to coincide with the isocenter for rotation of the C-arm based on the registration; and
   to derive at least one coordinate defining the position of the couch from the calculation.

8. The C-arm computed tomography system as claimed in claim 7, further comprising a screen, and where the control unit is designed to display on the screen all calculated coordinates to an operator.

9. The C-arm computed tomography system as claimed in claim 7, wherein the patient couch is moved by electric motors actuated by the control unit, and the control unit is designed to actuate the electric motors automatically such that the patient couch is then moved to the position specified by the calculated coordinate(s).

* * * * *